(12) United States Patent
Duc et al.

(10) Patent No.: US 11,039,910 B2
(45) Date of Patent: Jun. 22, 2021

(54) THREAD INSERTION DEVICES

(71) Applicant: Allergan Industrie SAS, Pringy (FR)

(72) Inventors: Antoine Duc, Saint Jean le Vieux (FR); Bastien Mandaroux, Metz-Tessy (FR)

(73) Assignee: Allergan Industrie SAS, Pringy (FR)

( * ) Notice: Subject to any disclaimer, the term of this patent is extended or adjusted under 35 U.S.C. 154(b) by 50 days.

(21) Appl. No.: 16/382,039

(22) Filed: Apr. 11, 2019

(65) Prior Publication Data
US 2019/0231503 A1 Aug. 1, 2019

Related U.S. Application Data

(62) Division of application No. 15/414,278, filed on Jan. 24, 2017, now Pat. No. 10,258,447.

(51) Int. Cl.
| | |
|---|---|
| *A61F 2/00* | (2006.01) |
| *A61B 17/062* | (2006.01) |
| *A61F 2/02* | (2006.01) |
| *A61F 2/10* | (2006.01) |
| *A61B 17/34* | (2006.01) |

(Continued)

(52) U.S. Cl.
CPC .......... *A61F 2/0059* (2013.01); *A61B 17/062* (2013.01); *A61F 2/02* (2013.01); *A61F 2/105* (2013.01); *A61B 17/06004* (2013.01); *A61B 17/06166* (2013.01); *A61B 17/3468* (2013.01); *A61B 2017/0042* (2013.01); *A61B 2017/0046* (2013.01); *A61B 2017/00336* (2013.01); *A61B 2017/00792* (2013.01); *A61B 2017/00898* (2013.01); *A61B 2017/00942* (2013.01); *A61B 2090/0801* (2016.02)

(58) Field of Classification Search
CPC ...................................... A61M 5/00

USPC ................... 623/23.72–23.74; 606/228–231; 604/110, 164.13, 165.01, 198

See application file for complete search history.

(56) References Cited

U.S. PATENT DOCUMENTS

| | | | |
|---|---|---|---|
| 1,250,114 A | 12/1917 | Bigelow et al. | |
| 1,558,037 A | 10/1925 | Morton | |

(Continued)

FOREIGN PATENT DOCUMENTS

| | | |
|---|---|---|
| EP | 0648474 | 4/1995 |
| EP | 0809968 | 12/1997 |

(Continued)

OTHER PUBLICATIONS

Bleyer, "SIS Facial Implant 510(k) Summary," Cook Biotech Inc. May 2005, 1 page.

*Primary Examiner* — Yashita Sharma
(74) *Attorney, Agent, or Firm* — Nathan S. Smith; Danny Mansour; Morgan, Lewis & Bockius LLP

(57) ABSTRACT

Devices and methods for inserting an implant into skin or other tissue of a patient can include an insertion device having moveable portions that can retain, move, or otherwise control engagement and injection of a hyaluronic thread. The device can include a tubular member and a handle. The handle can include a body component coupled to the tubular member. The body component can include a passage that extends in communication with the lumen. The handle can further comprise first and second arms coupled to the body component and extending outwardly from the distal portion of the tubular member. Based on the configuration, the first and second arms can be positioned along the passage to change a cross-sectional profile of the passage and permit the device to engage or disengage the thread.

18 Claims, 3 Drawing Sheets

(51) Int. Cl.
  *A61B 17/00*  (2006.01)
  *A61B 90/00*  (2016.01)
  *A61B 17/06*  (2006.01)

(56) References Cited

U.S. PATENT DOCUMENTS

| | | |
|---|---|---|
| 1,591,021 A | 7/1926 | Davis |
| 2,092,427 A | 9/1937 | Frederick |
| 2,302,986 A | 11/1942 | Vollrath |
| 2,571,653 A | 10/1951 | Victor |
| 3,204,635 A | 9/1965 | Voss |
| 3,674,026 A | 7/1972 | Werner |
| 3,910,282 A | 10/1975 | Messer et al. |
| 4,402,308 A | 9/1983 | Scott |
| 4,451,253 A | 5/1984 | Harman |
| 4,820,267 A | 4/1989 | Harman |
| 4,846,886 A | 7/1989 | Fey et al. |
| 4,957,744 A | 9/1990 | dellaValle et al. |
| 4,994,028 A | 2/1991 | Leonard |
| 5,116,358 A | 5/1992 | Granger et al. |
| 5,211,644 A | 5/1993 | VanBeek et al. |
| 5,215,535 A | 6/1993 | Gettig |
| 5,254,105 A | 10/1993 | Haaga |
| 5,258,013 A | 11/1993 | Granger et al. |
| 5,304,119 A | 4/1994 | Balaban |
| 5,350,385 A | 9/1994 | Christy |
| 5,366,447 A | 11/1994 | Gurley |
| 5,478,327 A | 12/1995 | McGregor et al. |
| 5,479,327 A | 12/1995 | McGregor et al. |
| 5,599,293 A | 2/1997 | Orenga |
| 5,735,827 A | 4/1998 | Adwers |
| 5,752,970 A | 5/1998 | Yoon |
| 5,824,335 A | 10/1998 | Dorigatti et al. |
| 5,997,513 A | 12/1999 | Smith |
| 6,102,920 A | 8/2000 | Sullivan |
| 6,159,233 A | 12/2000 | Matsuzawa |
| 6,162,203 A | 12/2000 | Haaga |
| 6,450,937 B1 | 9/2002 | Mercereau |
| 6,547,762 B1 | 4/2003 | Botich |
| 6,936,297 B2 | 8/2005 | Roby et al. |
| 7,041,088 B2 | 5/2006 | Nawrocki et al. |
| 7,504,386 B2 | 3/2009 | Pressato et al. |
| 7,559,952 B2 | 7/2009 | Pinchuck |
| 7,666,339 B2 | 2/2010 | Chaouk et al. |
| 7,722,582 B2 | 5/2010 | Lina et al. |
| 7,998,170 B2 | 8/2011 | Cunningham |
| 8,177,792 B2 | 5/2012 | Lubock |
| 8,652,216 B2 | 2/2014 | Chen |
| 9,214,030 B2 | 12/2015 | Sole et al. |
| 9,801,688 B2 | 10/2017 | Jones |
| 2001/0008937 A1 | 7/2001 | Callegaro et al. |
| 2001/0050084 A1 | 12/2001 | Knudson |
| 2002/0026039 A1 | 2/2002 | Bellini et al. |
| 2003/0023250 A1 | 1/2003 | Watschke |
| 2003/0097079 A1 | 5/2003 | Garcia |
| 2003/0109769 A1 | 6/2003 | Lowery |
| 2004/0192643 A1 | 9/2004 | Pressato et al. |
| 2005/0033362 A1 | 2/2005 | Grafton |
| 2005/0075606 A1 | 4/2005 | Botich |
| 2005/0182446 A1 | 8/2005 | DeSantis |
| 2006/0041320 A1 | 2/2006 | Matsuda |
| 2006/0136070 A1 | 6/2006 | Pinchuk |
| 2008/0119876 A1 | 5/2008 | Price et al. |
| 2008/0125766 A1 | 5/2008 | Lubock |
| 2008/0139928 A1 | 6/2008 | Lubock |
| 2008/0167674 A1 | 7/2008 | Bodduluri et al. |
| 2009/0131908 A1 | 5/2009 | McKay |
| 2009/0209804 A1 | 8/2009 | Seller |
| 2009/0318875 A1 | 12/2009 | Friedman |
| 2010/0256596 A1 | 10/2010 | Chomas |
| 2011/0093088 A1 | 4/2011 | Chen |
| 2011/0152926 A1 | 6/2011 | Vetrecin |
| 2011/0263724 A1 | 10/2011 | Gurtner |
| 2011/0282447 A1 | 11/2011 | Niu |
| 2012/0108895 A1 | 5/2012 | Neuman |
| 2012/0215230 A1 | 8/2012 | Lubock et al. |
| 2012/0245629 A1 | 9/2012 | Gross et al. |
| 2013/0122068 A1 | 5/2013 | Fermanian et al. |
| 2013/0211374 A1 | 8/2013 | Hetherington |
| 2013/0226235 A1 | 8/2013 | Fermanian et al. |
| 2013/0274222 A1 | 10/2013 | Horne et al. |
| 2013/0310750 A1 | 11/2013 | Hopman |
| 2014/0221940 A1 | 8/2014 | Clauson et al. |
| 2014/0228971 A1 | 8/2014 | Kim |
| 2015/0209265 A1 | 7/2015 | Horne |
| 2015/0209523 A1 | 7/2015 | Horne et al. |
| 2015/0327972 A1 | 11/2015 | Horne et al. |
| 2016/0007990 A1 | 1/2016 | Solish et al. |
| 2016/0074307 A1 | 3/2016 | Gurtner et al. |
| 2016/0213813 A1 | 7/2016 | Gurtner et al. |
| 2017/0049972 A1 | 2/2017 | Persons |
| 2017/0156754 A1 | 6/2017 | Valbuena |
| 2017/0290987 A1 | 10/2017 | Mandaroux et al. |
| 2018/0206963 A1 | 7/2018 | Duc et al. |
| 2018/0206964 A1 | 7/2018 | Duc et al. |
| 2018/0206965 A1 | 7/2018 | Duc et al. |
| 2018/0206966 A1 | 7/2018 | Duc et al. |
| 2018/0206967 A1 | 7/2018 | Duc et al. |

FOREIGN PATENT DOCUMENTS

| | | |
|---|---|---|
| EP | 2422832 | 2/2012 |
| EP | 2103262 | 2/2013 |
| EP | 2184016 | 4/2013 |
| EP | 2671516 | 12/2013 |
| GB | 2336783 | 5/2003 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| WO | WO 90/001349 | 2/1990 |
| WO | WO 92/013579 | 8/1992 |
| WO | WO 01/000190 | 1/2001 |
| WO | WO 2004/022603 | 3/2004 |
| WO | WO 2006/065837 | 6/2006 |
| WO | WO 2010/028025 | 3/2010 |
| WO | WO 2011/109129 | 9/2011 |
| WO | WO 2011/109130 | 9/2011 |
| WO | WO 2012/054301 | 4/2012 |
| WO | WO 2012/054311 | 4/2012 |
| WO | WO 2013/055832 | 4/2013 |
| WO | WO 2013/082112 | 6/2013 |
| WO | WO 2012/174464 | 5/2014 |
| WO | WO 2015/105269 | 7/2015 |

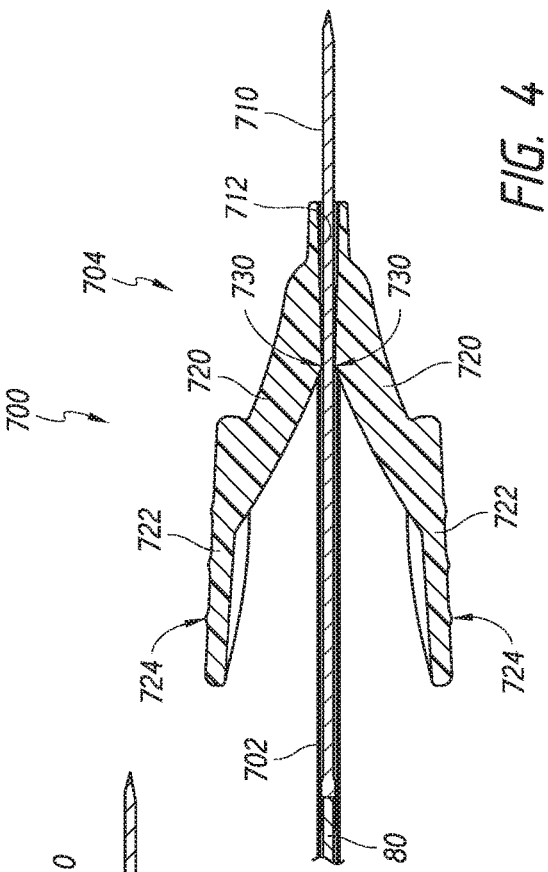
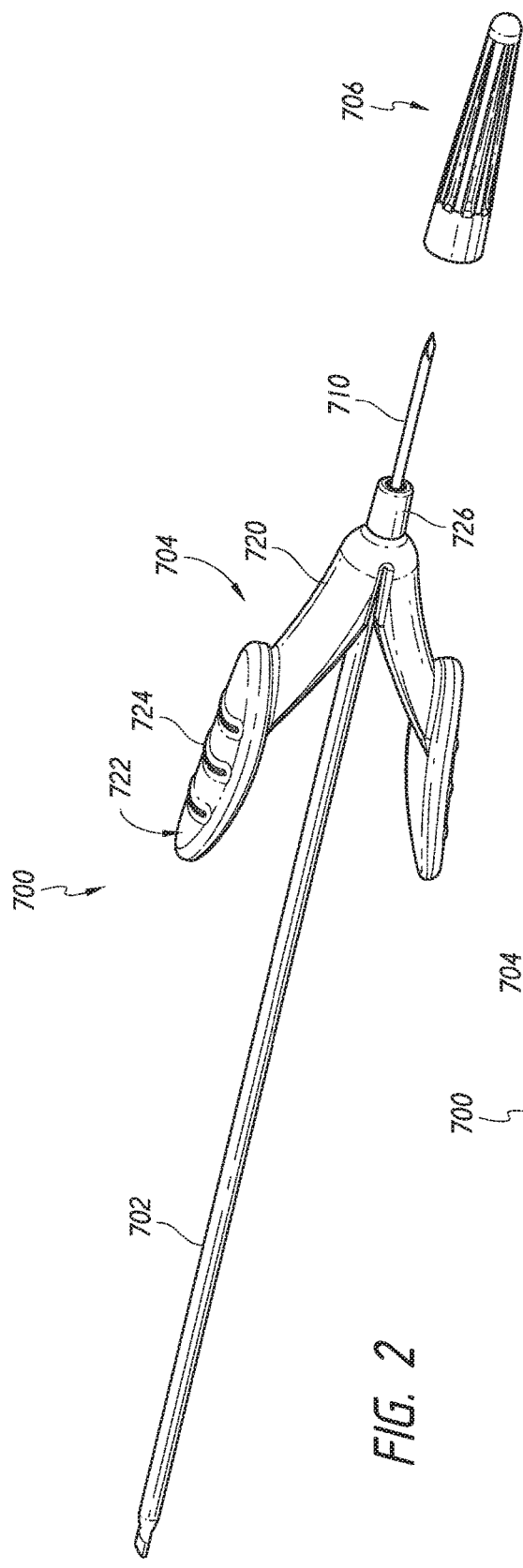
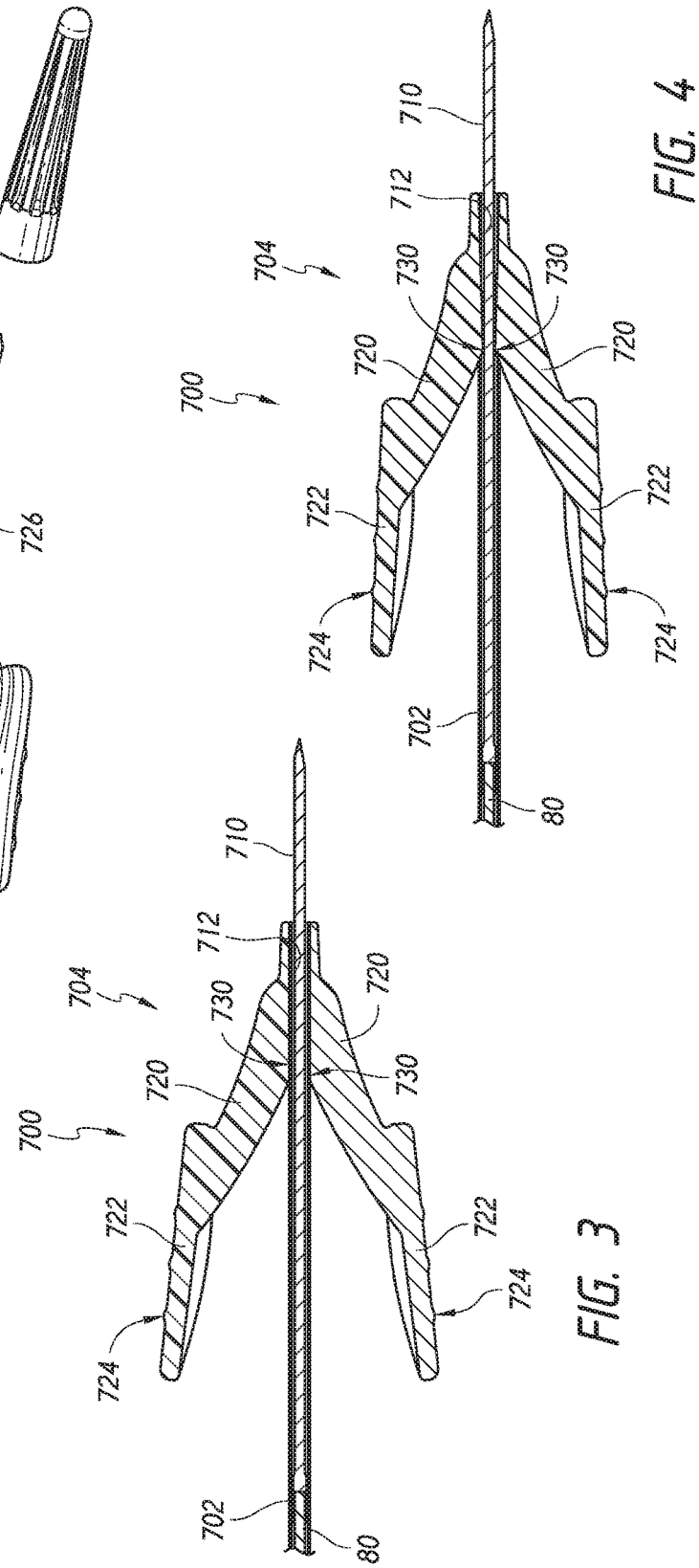
FIG. 2
FIG. 3
FIG. 4

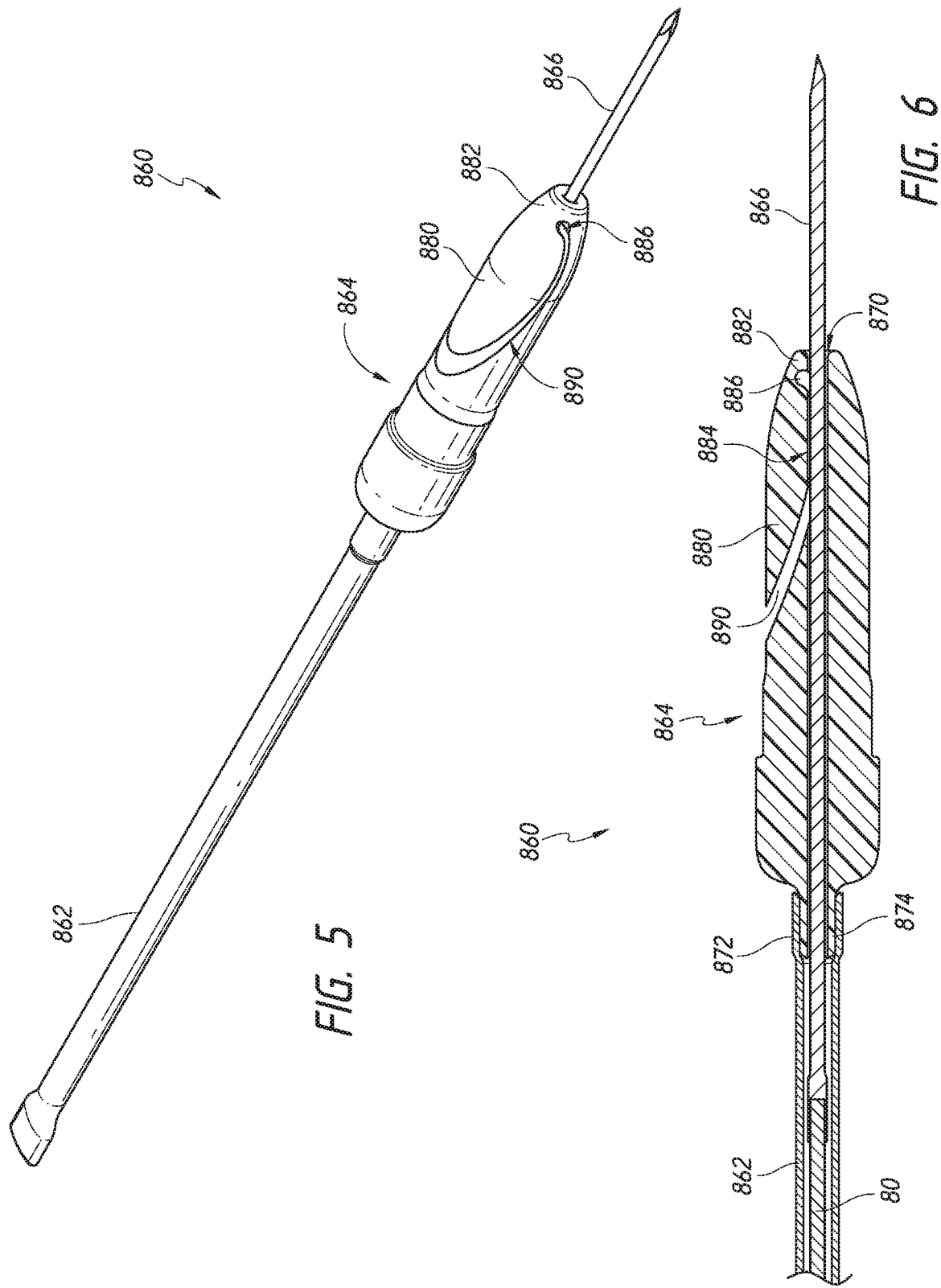

THREAD INSERTION DEVICES

CROSS-REFERENCE TO RELATED APPLICATIONS

This application is a divisional of U.S. patent application Ser. No. 15/414,278, filed Jan. 24, 2017, the disclosure of which is incorporated herein by reference in its entirety.

FIELD OF THE INVENTIONS

The present disclosure relates generally to systems and methods for insertion of an implant, and more particularly, to insertion devices that can protect and grasp a needle or thread to enable to physician to insert of the thread into skin or other tissue.

BACKGROUND

In recent years, millions of men and women have elected to receive dermal filler injections to rejuvenate aging skin and look younger without surgery or significant downtime. A dermal filler injection is a procedure through which a gel-like, volumizing substance is injected subcutaneously to restore lost volume, add volume to facial features and contours, or smooth fine lines and creases.

Some dermal filler injections are performed using a thread or other implant. Once inserted, the threads used for dermal filler injections can hydrate and expand or swell within the skin of a patient, thereby lessening the appearance of wrinkles, folds, and/or sagging portions of skin.

To insert a thread into the patient, conventional suture procedures can be implemented. For example, using a conventional procedure, a physician couples a thread to a needle and inserts the needle through the skin until achieving a desired placement, which may be adjacent to or under a wrinkle. With the thread placed along or underneath the wrinkle, the needle can be removed and as the thread hydrates, the wrinkle can be "filled" and become less prominent, thus smoothing the skin and achieving a desired aesthetic for the patient.

SUMMARY

The present application discloses various improvements for thread insertion devices and related procedures that can be used to treat humans and/or animals. The devices and procedures can be used, for example, in the context of dermal fillers, surgery (e.g., placing sutures), drug delivery, negative pressure wound therapy, and wound dressing.

In plastic surgery, hyaluronic acid is a common substance used for wrinkle filling. Although hyaluronic acid is typically used as a gel that is injected as a wrinkle filler, some embodiments disclosed herein can utilize hyaluronic acid in a solid form as an implant, e.g., as a hyaluronic acid thread ("HA thread" or "thread").

However, in accordance with some embodiments disclosed herein in the realization that because HA threads are hydrophilic, the mechanical integrity of the thread can rapidly degrade during an implantation procedure. Thread failure can result in improper placement or other complications during the procedure. Thus, a thread that is exposed during insertion of the thread into a patient can become hydrated, causing the thread to swell or expand prematurely and/or lose its tensile strength. If the thread swells within a needle or insertion device, the thread will become lodged within the needle and unable to move relative to the insertion device. The thread can therefore block the needle lumen, prevent separation of the thread from the insertion device, or otherwise complicate the thread placement procedure. In some instances, the swelling of a thread may cause it to engage with skin tissue before the thread has reached a desired position subcutaneously. Thus, the thread becomes immovable during insertion of the thread into the patient. Further, during insertion, friction between the thread and the tissue may increase beyond a tensile strength of the thread and cause the thread to break and separate from the insertion device.

Further, some embodiments of the present devices and methods also contrast with various conventional thread placement devices that include a needle tip that engages a thread at its midsection and allows the thread to fold backwardly or proximally along a length of the needle. In accordance with some embodiments disclosed herein in the realization that because the thread is divided into two strands that extend along the length of the needle, the injection also results in a double-stranded thread placement in which the two strands will swell in situ. Although this may be acceptable in some applications, these conventional devices and procedures are limited because they have a "minimum expansion size" of twice that of a single thread. Accordingly, some of the embodiments disclosed herein enable a single strand of thread to be placed along a desired position instead of the conventional double-stranded thread placement. Advantageously then, some embodiments allow for a lower "minimum expansion size" that can allow a physician to treat wrinkles that are not otherwise good candidates for treatment using only the conventional devices or methods.

Further, because some embodiments disclosed herein "push" a distal end of the thread through the skin, the physician need only to make a single piercing instead of entry and exit piercings required by conventional devices and methods that use a needle whose proximal end attaches to a distal end of the thread and pulls the thread through the entry and exit piercings.

Therefore, some embodiments of the thread insertion devices and procedures disclosed herein can advantageously minimize the number of piercings through the skin, reduce the risk of thread contamination during the insertion procedure, and/or minimize pain and bruising to the patient. Further, some embodiments of the thread insertion devices and procedures disclosed herein can advantageously avoid breakage of the thread during insertion, facilitate safer and easier insertion of the thread, and/or permit greater control over the thread length and insertion depth.

Although particular embodiments of the present disclosure may be disclosed in the context of an implant comprising a thread, it is contemplated that embodiments can be used with various implants. For example, embodiments can be used with an implant comprising a thread, a series of hinged members, or a tube. Further, embodiments can comprise an implant comprising a rigid material, a flexible material, HA threads material, and a material comprising a state of matter including solid, liquid, or any state there between. The implant can comprise a medication and/or medical fluid that are configured to be released by the implant.

In some embodiments, the thread insertion device can comprise a cover member configured to protect an implant, or portions of a device that will be inserted into a patient. The cover member can prevent contamination or damage to a thread. The cover member can also maintain a shape or alignment of a thread relative to a thread insertion device.

The cover member can comprise a cavity or passage configured for a thread to be positioned therein. For example, the cover member can retain at least a portion or an entirety of the thread within a cavity or passage. Contamination or damage to the thread can be prevented when the thread is positioned within a cavity or passage of the cover member. The cover member can prevent contamination of the thread from exposure to an ambient environment, or from a person touching the thread. Further, damage to the thread can be avoided by preventing inadvertent touching or engagement of the thread. Damage to the thread can also be avoided by preventing exposure of the thread to moisture from the patient's skin or tissue, e.g., dermis, epidermis, and subcutaneous tissue, during insertion of the thread.

In some embodiments, the cover member can permit a thread to be positioned along an outer surface of the cover member. The cover member can permit a thread to be positioned along an inner surface of the cover member. The cover member can also provide support to maintain alignment of the thread during insertion.

In some embodiments, the thread can be retained and/or engaged with the cover member and/or a portion of the thread insertion device. Further, the cover member and/or a portion of the thread insertion device can be used to move a thread relative to the insertion device or separate a thread from the insertion device.

For example, the insertion device can comprise one or more portions that extend along an outer surface and/or within the cover member. The thread insertion device can comprise a moveable member within the cover member. A piston can be positioned within a cavity of the cover member. The piston can cause movement of the thread supported on or coupled with the insertion device. Movement of a portion of the insertion device, e.g., the cover member and/or the piston, can release or separate a thread from the insertion device.

In some embodiments, the thread insertion device can comprise a cover member that can be engaged against a thread to retain the thread with the insertion device. A portion of the cover member can be crimped, or compressed, or adhered to engage a portion of a thread. The thread can be adhered to the cover member. To release a thread from the insertion device, a portion of the cover member engaged against a thread can be moved or expanded, or the thread can be separated from the portion of the cover member.

The cover member can comprise a flexible or rigid body. The body can comprise a cross-sectional profile that defines a cavity. A shape of a cross-sectional profile of the cover member can comprise an open perimeter, a closed perimeter, a circle, a square, a rectangle, an L-shape, and/or a U-shape. The cover member can comprise an inner surface cross-sectional profile having portions that are tubular along a length of the cover member.

A portion of the cover member can comprise an opening, e.g., a channel or an aperture, between an inner cavity and an outer surface of the cover member. The cover member can permit a thread to be moved through the opening. A thread can be coupled to the insertion device by a portion of the thread that extends through the opening.

The cover member can comprise a proximal portion and a distal portion. The proximal portion can comprise an opening into a cavity of the cover member. The proximal portion can be coupled to other portions of the thread insertion device. The proximal portion can be releasably coupled to a portion of the insertion device.

A cavity of the cover member can extend toward the distal portion of the cover member. The cavity can extend toward a closed distal portion of the cover member. The distal portion of the cover member can comprise a tip portion. The tip portion can comprise an outer surface that tapers toward a point. A tapered or pointed tip can permit the cover member to pierce the patient's skin or tissue to allow insertion of the cover member and thread. The tip can comprise a point, a bevel, or a multiple-sided cutting point, e.g., a pin, a needle, or a trocar. The tip portion can comprises an outer surface that is rounded or blunt. A round or blunt tip can permit insertion of the cover member through an opening of a patient without piercing or causing damage to the patient.

The thread insertion device can comprise a handle to engage or release a portion of the insertion device. The handle can be moved, relative to the insertion device, to engage or release a portion of the insertion device. A portion of the handle can be configured to be held by a physician and moved relative to the insertion device.

A needle can be positioned within the insertion device between portions of the handle. Movement of the handle can cause a portion of the insertion device to engage the needle. The needle can comprise a proximal portion and a distal portion, opposite the proximal portion. The needle can be positioned with the proximal portion between portions of the handle, and the distal portion extending from the insertion device. A thread can be coupled to the proximal portion of the needle.

The handle can comprise a moveable portion configured to be urged or move relative the handle or the insertion device. The moveable portion can comprise an arm, a lever, a button, and/or a moveable member. The moveable portion can be urged toward or away from the insertion device. Urging the moveable portion toward the insertion device can cause a portion of the handle to extend into a lumen of the insertion device. Urging the moveable member toward the insertion device can cause a portion of the handle to move away from a lumen of the insertion device.

The handle can comprise a moveable member configured to intersect a lumen that extends through the handle. The moveable member can be positioned to engage a needle positioned within the lumen, thereby preventing movement of the needle along an axial length of the lumen. The moveable member can be moved to disengage from the needle and permit movement of the needle along an axial length of the lumen.

The handle can comprise an arm to permit and/or prevent movement of a needle relative to the insertion device. The arm can extend from the insertion device, and can be moved by urging the arm toward or away from the insertion device. A portion of the arm or handle can engage a needle positioned within the insertion device when the arm is urged, thereby preventing movement of the needle relative to the insertion device. Optionally, a portion of the arm or handle can release a needle positioned within the insertion device when the arm is urged, thereby permitting movement of the needle relative to the insertion device.

The handle can comprise first and second arms that extend from the insertion device. A portion of the first and second arms can engage a needle positioned within the insertion device when the first and second arms are urged toward each other. Each arm of the handle can comprise a first portion that extends away from the insertion device, and a second portion, e.g., a gripping mechanism, that extends from the first portion toward the insertion device. The gripping mechanism of each arm can overlap each other and intersects a lumen of the insertion device. In a first configuration, the first and second arms can be biased away from each other to engage a needle within the lumen. In a second configuration, the first and second arms can be urged further toward each other to release the needle within the lumen.

The thread insertion device can comprise a tubular member to prevent contamination or damage to a thread and/or needle. The tubular member can maintain a shape or alignment of a thread relative to a thread insertion device. The tubular member can comprise an envelope, a sleeve, and/or a cavity configured to retain a thread therein. The tubular member can comprise a rigid material, flexible material, and/or a heat-shrinkable material.

The tubular member can be a tube configured to restrict movement of a thread, positioned within the tubular member, along a longitudinal axis of the thread. The tubular member can comprise an inner cross-sectional profile approximately equal to a cross-sectional profile of a thread to permit movement of the thread within the tubular member. The tubular member can comprise a cavity to permit a thread to be gathered within the cavity. As the thread, or needle coupled to the thread, can be directed away from the insertion device, the portion of the thread gathered within the cavity can be withdrawn from the tubular member.

The tubular member can be formed as a portion of the insertion device or coupled to the insertion device. Optionally, a portion of the tubular member can comprise a portion of a handle. The tubular member can comprise a proximal portion and a distal portion, opposite the proximal portion. The distal portion can be coupled to the insertion device to form a cavity that extends from the insertion device toward the tubular member. The distal portion can be coupled to a handle or a base of the insertion device. Optionally, the tubular member can comprise a cover member.

The thread insertion device can comprise a cap to enclose a portion of a thread or a needle. The cap can be removably coupled with a handle to enclose a portion of a needle extending from a handle, thereby preventing inadvertent contact or contamination of the needle.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures:

FIG. 2 is a front perspective view of an insertion device, according to some embodiments.

FIGS. 3 and 4 are cross-sectional side detail views of an insertion device, according to some embodiments.

FIG. 5 is a front perspective view of an insertion device, according to some embodiments.

FIG. 6 is a cross-sectional side detail view of an insertion device, according to some embodiments.

DETAILED DESCRIPTION

Figure 1:
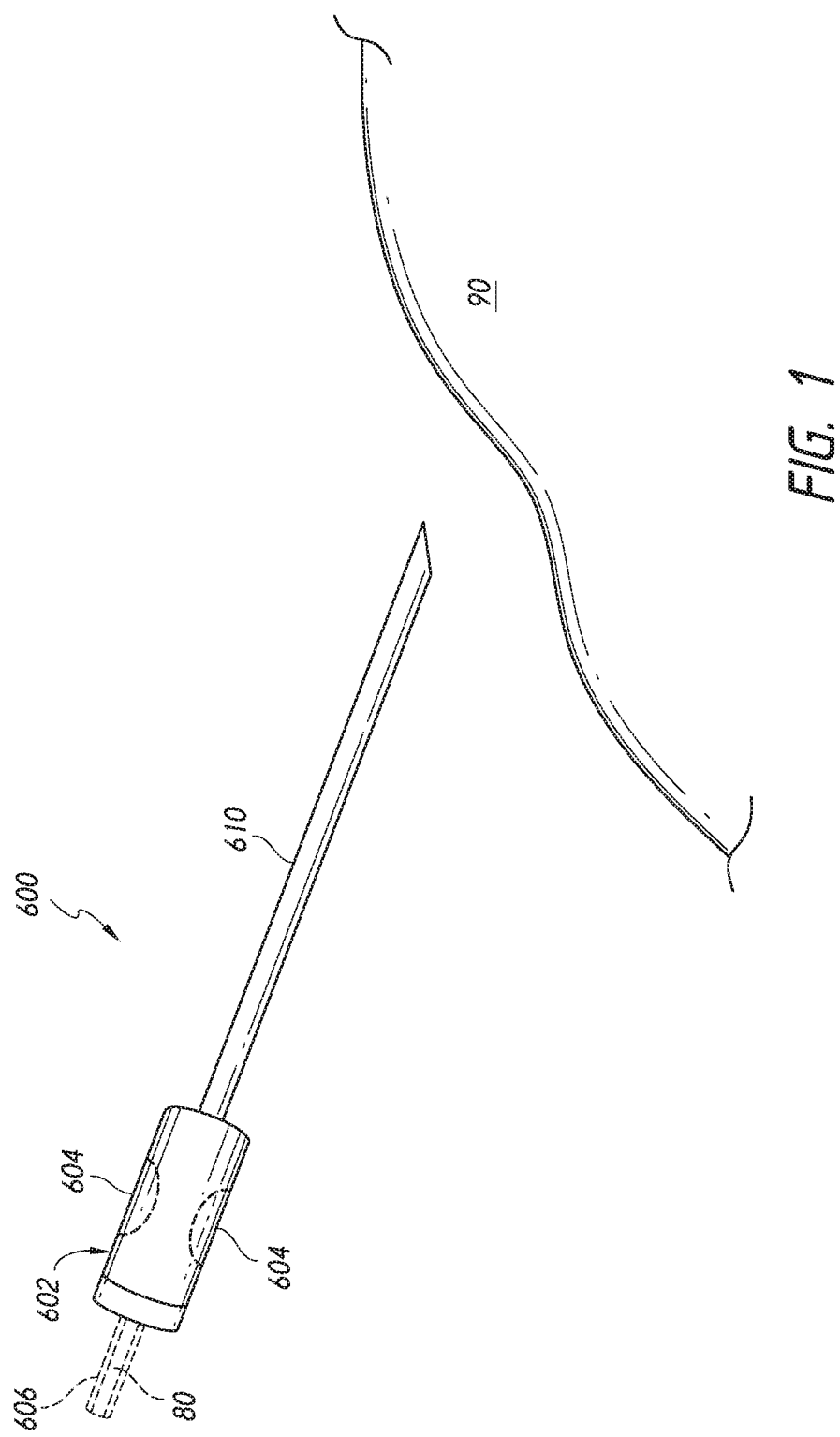
FIG. 1 is a front view of an insertion device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of HA thread insertion devices, such embodiments can be used with various devices and implants. Furthermore, various applications of such embodiments and modifications thereto, which may occur to those who are skilled in the art, are also encompassed by the general concepts described herein.

The present application addresses several operational challenges encountered in prior HA thread insertion devices and related procedures. This application provides numerous improvements that enable the physician to control the device more easily, thereby allowing precise positioning of the implant while minimizing trauma to the patient.

For example, in accordance with some embodiments, the present application discloses various features and advantages of thread insertion devices and procedures that can be used to deliver an implant into skin or other tissue of a patient. The thread insertion device can avoid contamination of an HA thread and can protect the thread's mechanical properties during insertion. The thread insertion device can also permit a physician to precisely position the implant while minimizing trauma to the patient. The present disclosure, along with co-pending U.S. patent application Ser. No. 15/414,195 (19928 (COR) (122320-5003)), U.S. Ser. No. 15/414,248 (20294 (COR) (122320-5004)), U.S. Ser. No. 15/414,219 (20296 (COR) (122320-5013)), and U.S. Ser. No. 15/414,306 (20298 (COR) (122320-5014)), each entitled "THREAD INSERTION DEVICES," and each filed on the same day as the present application, includes various features that can be interchangeably implemented into embodiments of thread insertion devices and methods of their use and the contents of these applications are incorporated herein in by reference in their entireties. For example, various aspects of the engagement mechanisms, actuation components, cover members, handles, and other features for delivering, protecting, engaging, advancing, or otherwise handling a needle and/or thread, can be combined or substituted with features of embodiments disclosed herein.

Further, some embodiments of the thread insertion devices and procedures disclosed herein can advantageously allow a single strand of HA thread to be positioned in situ as opposed to conventional double-stranded thread placement. In some embodiments, needle insertion devices can be provided that can engage a needle and/or thread in order to permit a physician to advance the needle and/or thread into a patient.

As discussed above, a HA thread can be used as a dermal filler to treat wrinkles. This solution is of particular interest to treat long and thin wrinkles in very localized and continuous manner. HA threads could be used on various points of correction on the neck, face, décolletage, hands, or other such areas.

In some embodiments, thread insertion procedures can be performed using a needle or trocar directly attached to a HA thread in a suture-like arrangement. The HA thread can be placed linearly under the wrinkle and pulled through the skin in a suture-like process using the needle. The injection requires the needle to pierce the skin at an entry point, to be advanced subcutaneously until the thread is pulled and positioned subcutaneously, and then to pierce the skin a second time at an exit point to withdraw the needle. The thread and the needle can be separated by twisting the wired thread until it breaks.

The present disclosure provides an a variety of needle insertion devices that provide greater control, ease of use, reduced risk of contamination, and better protection of the thread than prior devices and procedures. For example, some of the needle insertion devices disclosed herein can enable a physician to securely grasp the needle using a device, separated from the thread, which is releasably attachable to the needle. Some embodiments of the devices can move between a first configuration in which components of the device are positioned along a passage wherethrough the needle or trocar passes to define a first cross-sectional clearance, and a second configuration in which a portion of at least one of the components extends into, compresses, or otherwise obstructs the passage to define a second cross-sectional clearance, different from the first cross-sectional clearance, to thereby change a cross-sectional profile of the passage. The first cross-sectional clearance can be less than or greater than the second cross-sectional clearance, which can allow needle to be selectively engaged by the components of the device.

For example, referring now to FIG. 1, a schematic illustration of an embodiment of a needle or thread insertion device 600 is illustrated. The insertion device 600 can comprise a handle 602, a moveable portion 604, and a tubular member 606. The tubular member 606 can be coupled to a proximal end of the handle 602. The needle 610 can be coupled at its proximal end to a HA thread 80 that extends within the tubular member 606. Further, a trocar or needle 610 can extend through a passage of the handle 602 to be releasably engaged by the moveable portion 604 to permit or restrict movement of the needle 610 relative to the handle 602 and the tubular member 606.

In accordance with some embodiments, the handle 602 can be configured to engage with the needle 610 and/or the thread 80 to permit the physician to advance the needle 610 into the patient and thereafter release the needle 610 and/or the thread 80.

The handle 602 can comprise a passage that extends through proximal and/or distal portions of the handle 602. The tubular member 606, the needle 610, and/or the thread 80 can extend through the passage of the handle 602. As discussed further herein, the size of the passage can be changed, e.g., increased or reduced, to selectively engage or release the tubular member 606, the needle 610, and/or the thread 80 extending through the passage to permit movement of the needle 610 and/or the thread 80 through the passage, relative to the insertion device 600.

The needle 610 can have a proximal portion and a distal portion. The distal portion of the needle 610 can comprise an outer surface that tapers toward a pointed tip to pierce the tissue and/or skin 90 of a patient. The distal portion of the trocar 610 can also comprise a rounded or blunt surface. Further, as noted above, the needle 610 can comprise a trocar having a three-sided cutting point or tip.

A portion of the thread 80, e.g., a distal portion, can be attached or coupled to the proximal portion of the needle 610. For example, the proximal portion of the needle 610 can comprise a cavity or pocket. The cavity can receive and be coupled to a distal portion of the thread 80. The thread 80 can be coupled to the needle 610 mechanically or by using an adhesive such as, for example, glue, tape, or other solutions to engage the proximal portion of the needle 610 with the thread 80.

The tubular member 606 can enclose, house, or be coupled to a portion of a needle and/or the thread 80. For example, the tubular member 606 can comprise a tube, an envelope, and/or a sleeve that defines an inner surface and lumen that extends between proximal and/or distal portions of the tubular member 606. The lumen can be configured to permit the needle 610 and/or thread 80 to be positioned therein. In some embodiments, the cavity of the tubular member 606 can be used to protect the thread 80 from contamination prior to and during the injection procedure. Additionally, the tubular member 606 can permit the thread to be stored or gathered within a cavity of the tubular member 606. Further, the tubular member 606 can comprise a rigid material, flexible material, and/or a heat-shrinkable material.

The lumen of the tubular member 606 can have a cross-sectional profile, transverse to the longitudinal axis of the tubular member 606, which can comprise a circle, oval, regular or irregular polygon, square, and/or rectangle shape. The cross-sectional profile of the tubular member 606 can have a size that is at least approximately equal to an outer cross-sectional profile of the needle 610 and/or thread 80 to permit movement of the thread 80 and/or needle within the tubular member 606 (when not crimped or constricted).

The insertion device 600 can be actuated to engage or disengage with the needle 610 and/or the thread 80 using the handle 602. The handle 602 can be disposed at a distal portion of the tubular member 606. In some embodiments, the handle 602 can be formed with the tubular member 606 as a single component or unitarily as a single, continuous piece of material. However, as illustrated, the handle 602 can be formed as a separate component that is coupled to the tubular member 606. The handle 602 can be configured to extend along the lumen or a portion of the outer surface of the tubular member 606.

In some embodiments, the handle 602 can comprise at least one moveable portion 604. The movable portion 604 can comprise an arm, lever, button, and/or movable member that can be deflected or moved by the physician relative to the passage of the handle 602 to decrease or increase the size of the passage. The change in size of the passage of the handle 602 thereby directly or indirectly engages or disengages the device 600 with the tubular member 606, the needle 610, and/or the thread 80. In some embodiments, the moveable portion 604 can be formed unitarily (e.g., from a single, continuous piece of material) with the handle 602 or can be a separate component that can be coupled to the handle 602. The moveable portion 604 can comprise first and second movable portions that are moveable relative to each other.

For example, in some embodiments, compressing the moveable portion(s) 604 toward a longitudinal axis of the insertion device 600 can cause a portion of the movable portion 604 and/or the handle 602 to be urged toward and/or into the passage to engage with the needle 610, the tubular member 606, and/or the thread 80.

However, in other embodiments, compressing the moveable portion(s) 604 toward a longitudinal axis of the insertion device 600 can cause a portion of the movable portion 604 and/or the handle 602 to extend out of the passage to permit the needle 610, the tubular member 606, and/or the thread 80 to move freely within the passage and/or to become disengaged from the handle 602.

Further, in some embodiments in which the tubular member 606 extends at least partially through the passage of the handle 602, the movable portion 604 can engage with or release the tubular member 606 to crimp down onto or release the needle 610 and/or thread 80 disposed within the lumen of the tubular member 606. For example, the tubular member 606 can be deflected, crimped, and/or resiliently move between a clear-through lumen state and constricted lumen state to permit or restrict movement of a thread or needle positioned therein along a longitudinal axis of the thread.

Accordingly, the physician can selectively actuate the movable portion 604 of the handle 602 in order to engage or disengage the needle 610 and/or thread 80 during the injection procedure.

FIGS. 2-4 illustrate an embodiment of the needle insertion device that can be pinched to engage the needle, thereby allowing a physician to advance the needle to a desired position in situ, and later release compression or pinching of the device to release the needle. As shown, and as similarly discussed above with regard to the insertion device 600, FIGS. 2-4 illustrate an insertion device 700 that comprises a tubular member 702, a handle 704, a cap 706, and a needle 710 extending through a passage of the device 700. When a physician desires to grip and advanced the needle during an injection procedure, the insertion device 700 can be pinched to engage the needle 710. The insertion device 700 can incorporate various features discussed above with respect to the insertion device 600, the entire details of which will not be discussed here for brevity.

The tubular member 702 can enclose, house, or be coupled to a portion of a needle and/or a HA thread 80. The tubular member 702 can be coupled to the handle 704 or be formed therewith. For example, the tubular member 702 can comprise a tube, an envelope, and/or a sleeve that defines an inner surface and lumen that extends between proximal and/or distal portions of the tubular member 702. The lumen can be configured to permit the needle 710 and/or thread 80 to be positioned therein. In some embodiments, the cavity of the tubular member 702 can be used to protect the thread 80 from contamination prior to and during the injection procedure. A proximal portion of the tubular member 702 can be crimped, compressed, or glued to close the proximal portion of the lumen.

The lumen of the tubular member 702 can have a cross-sectional profile, transverse to the longitudinal axis of the tubular member 702, which can comprise a circle, oval, regular or irregular polygon, square, and/or rectangle shape. The size of the cross-sectional profile of the tubular member 702 can be at least approximately equal to a cross-sectional profile of the thread 80 and/or the needle 710 positioned therein. The lumen can permit axial and rotational movement of the thread 80 and needle 710, relative to the longitudinal axis of the lumen. The shape or size can vary along the length or width of the tubular member 702.

The handle 704 can be positioned along the distal portion of the tubular member 702. The handle 704 can comprise a proximal portion, a distal portion, and a longitudinal axis between the proximal and distal portions. The handle 704 can also comprise a passage 712 that extends between the proximal and distal portions of the handle 704. The passage 712 can be aligned with respect to the longitudinal axis of the handle 704. In some embodiments, the tubular member 702 can extend at least partially through the passage 712 of the handle 704. The tubular member 702 can also extend only partially through the passage 712 of the handle 704. For example, a distal portion of the tubular member 702 can be coupled with the proximal portion of the handle 704 so that the lumen of the tubular member 702 extends continuously with the passage 712. However, in some embodiments, the tubular member 702 can extend through an entirety of the passage 712 of the handle 704.

Further, in some embodiments, a pass-through clearance for the needle can be changed in order to selectively engage or release the tubular member, the needle, and/or the thread extending through the passage to permit or restrict movement of the needle and/or the thread through the passage, relative to the insertion device. For example, in some embodiments, the size of the passage 712 can be changed, e.g., increased or reduced, to selectively engage or release the tubular member 702, the needle 710, and/or the thread 80 extending through the passage to permit or restrict movement of the needle 710 and/or the thread 80 through the passage 712, relative to the insertion device 700. The change of the size of the passage 712 can pinch down onto the needle 710, as shown in FIG. 4, and allow the physician to advance the needle 710 into the patient and thereafter release the needle 710 and/or the thread 80 by releasing compression on the passage 712, thereby permitting the needle 710 and/or the thread 80 to move relative to the handle 704.

As shown in FIGS. 3 and 4, the handle 704 can comprise at least one moveable portion 720. The movable portion 720 can be movable to deflect into or otherwise change the size of the passage 712. For example, the movable portion 720 can comprise an arm, lever, button, and/or movable member that can be deflected or moved by the physician relative to the passage 712 of the handle 704 to decrease or increase the size of the passage. In some embodiments, the movable portion 720 can be configured as an arm or cantilevered tab. The arm 720 can be configured to be biased toward an open position.

For example, the arms 720 can be biased toward an open position that provides a clear-through lumen state, and the arms 720 can be deflected or pinched to overcome the biasing force and constrict the size of the passage 712, as discussed further below.

Each arm 720 can comprise a first portion coupled to the handle 704 and a second portion that extends outwardly from the handle 704. In accordance with some embodiments, the handle 704 can comprise first and second arms 720, as shown in FIGS. 3 and 4. The first and second arms 720 can extend outwardly from the tubular member 702 in opposing directions. Although the handle 704 can comprise first and second arms 720, a single arm 720 is described herein for clarity and brevity.

Further, the embodiment of the insertion device 700 illustrates that the arm 720 and the handle 704 can be formed unitarily as a single, continuous component. However, the arm 720 can also be a component that is separate from the handle 704 and can be coupled to the handle 704. Thus, while the handle 704 can be injection molded as a single piece that includes the arms 720 joined to a body component 726 to form the entirety of the handle 704, the handle 704 can also be formed by coupling independent, separate components together. For example, the handle can be formed by coupling one or more arms 720 together form the passage 712 therebetween or by coupling one or more arms 720 together with the body component 726.

In accordance with some embodiments, the arm 720 can comprise a grasping member 722 that can be gripped by the physician. The grasping member 722 can be disposed along and extend from a distal portion of the arm 720, transverse to a longitudinal axis of the arm. The grasping member 722 can have a grasping surface 724 that faces away from the tubular member 702. The grasping surface 724 can comprise a concave, convex, and/or planar surface. For example, the grasping surface 724 can comprise a ridge, groove, and/or textured surface.

In some embodiments, as shown in FIGS. 3 and 4, compressing the moveable portions or arms 720 toward a longitudinal axis of the insertion device 700 decrease the size of the passage 712 to engage with the needle 710, the tubular member 702, and/or the thread 80 disposed therein.

For example, the handle 704 can comprise one or more engagement surfaces 730 that extend adjacent to or within the passage 712. In embodiments comprising first and second arms 720, the handle 704 can comprise opposing engagement surfaces 730. The engagement surface 730 can be formed as a portion of the arm 720 adjacent to the passage 712. However, the engagement surface 730 can also be formed on a component that is separate from the handle 704 and can be coupled to the handle 704.

Compression of the moveable portions or arms 720 toward a longitudinal axis of the insertion device 700 can cause the engagement surfaces 730 to be urged toward and/or into the passage 712 to engage with the needle 710, the tubular member 702, and/or the thread 80 disposed therein. In some embodiments, the engagement surfaces 730 can at least partially define an inner boundary or aspect of the passage 712. When the engagement surfaces 730 are compressed or actuated toward and/or into the passage 712, the passage 712 can have a reduced cross-sectional profile or dimension at the location along which the engagement surfaces 730 are positioned.

Further, in some embodiments in which the tubular member 702 is disposed within the passage 712, the engagement surfaces 730 can deflect, crimp, and/or resiliently move the tubular member 702 between a clear-through lumen state and constricted lumen state to permit or restrict movement of the thread 80 or the needle 710 positioned therein.

The insertion device 700 can move between a disengaged configuration and an engaged configuration. In the disengaged configuration, shown in FIG. 3, the engagement surface 730 is positioned outside of or spaced apart from the passage 712 of the handle 704 to be disengaged from the tubular member 702, the needle 710, and/or the thread 80. Thus, the needle 710 is freely movable within the passage 712. Further, the thread 80, which is coupled to the needle 710, is also freely movable and extends within the tubular member 702.

Further, in the disengaged configuration, illustrated in FIG. 3, the opposing engagement surfaces 730 of each respective arm can be separated by a first distance. The first distance can be approximately equal to or greater than the outer cross-sectional profile of the tubular member 702 or a clear-through or fully open inner cross-sectional profile of the passage 712 (i.e., the cross-sectional profile of the passage 712 when the passage 712 is not constricted). The first distance can be approximately equal to or greater than to a diameter of the thread 80 or needle 710.

In the engaged configuration shown in FIG. 4, which illustrates an embodiment in which the tubular member extending into the passage 712, the engagement surface 730 can compress or be crimped down against the outer surface of tubular member 702, thus engaging the tubular member 702 and the needle 710 and restricting longitudinal movement of the needle 710 within the passage 712. For example, in the engaged configuration, the opposing engagement surfaces 730 of each respective arm can be separated by a second distance. The second distance can be less than the outer cross-sectional profile of the tubular member 702 or the clear-through or fully open inner cross-sectional profile of the passage 712. The second distance can be approximately equal to or less than a diameter of the thread 80 or needle 710. A portion of at least one of the first or second arm 720 can extend into the passage 712 to decrease a cross-sectional profile of the passage 712 in the engaged configuration.

In an injection procedure, to insert the needle 710 and thread 80 into the patient, the insertion device 700 can be pinched or actuated to the engaged configuration by moving or biasing the arms 720 toward the tubular member 702, such that the engagement surface 730 of the arms engages the needle 710. The insertion device 700 can then be directed toward a patient's skin so that the distal portion of the needle 710 pierces the skin and permits movement of the needle 710 into the patient.

After the needle 710 has been advanced partially into the skin, the physician can release engagement between the insertion device 700 and the needle 710 in order to proximally retract the insertion device 700 relative to the needle 710 and engage the needle 710 at a second, more proximal position than the initial position at which the device 700 was engaged. Thus, further insertion of the needle 710 and thread 80 into the patient can be achieved by returning the insertion device 700 to the disengaged configuration by releasing the arms to permit the engagement surface 730 to move away from the tubular member 702. The insertion device 700 can then be moved toward the proximal portion of the needle 710 and the arms be pinched toward the tubular member 702, such that the engagement surface 730 of each arm engages the needle 710.

The insertion device 700 can be configured so that the needle 710 is inserted through a first portion of the skin and removed through a second portion of the skin. In operation, the needle 710 can be moved through the first portion of the skin using the insertion device 700 until the distal portion of the needle 710 extends through the second portion of skin. The needle 710 can then be withdrawn from the patient and the handle can be retracted relative to the patient. Any portion of the thread 80 that remains extending through the surface of the patient's skin can be separated or cut so that the remaining portion is entirely within the patient's skin.

The insertion device 700 can comprise a cap 706 that can be coupled to the handle 704 and enclose a portion of the thread 80 or the needle 710. The cap 706 can comprise a cavity that extends from a proximal portion toward a distal portion. The outer surface of the cap 706 can taper from the proximal portion toward the distal portion. The cap 706 is coupled to the handle 704 by inserting the distal portion of the handle 704 into the cavity of the cap 706. The cross-sectional profile of the outer surface of the handle 704 and the inner surface of the cap 706 can be configured to provide a friction fit between the handle 704 and the cap 706.

The cap 706 can be coupled to the insertion device 700 in the disengaged or engaged configuration, and with our without the thread 80 and needle 710 positioned therein. The insertion device 700 can comprise the cap 706 coupled to the handle 704 with the thread 80 and needle 710 positioned therein, such that a physician removes the cap 706 prior to operation if the insertion device 700. The cap 706 can comprise any of the features of a support member or cover member described in the present application.

Referring now to FIGS. 5 and 6, additional embodiments of insertion devices employing engagement mechanisms similar to those discussed above with regard to the embodiment shown in FIGS. 1-4 are shown.

For example, FIGS. 5 and 6 illustrate an insertion device 860 that comprises a tubular member 862 coupled to a handle 864. Similar to the embodiment illustrated above with respect to FIGS. 1-4, the handle 864 can comprise a moveable portion that can be actuated to engage and/or release a needle 866 that is coupled to a HA thread 80.

The tubular member 862 can comprises a proximal portion, a distal portion, and a longitudinal axis between the proximal and distal portions. The tubular member 862 can be a tube with a cavity or lumen that extends from the distal portion toward a closed proximal portion.

The handle 864 can comprise a proximal portion, a distal portion, and a longitudinal axis between the proximal and distal portions. The handle 864 can also comprise a passage or lumen 870 extends through the handle 864, between the proximal and distal portions. The lumen 870 can be aligned with respect to the longitudinal axis of the handle 864.

The handle 864 can be coupled with the tubular member 862. For example, as shown in FIG. 5, a distal portion 872 of the tubular member 862 can be coupled with the proximal portion 874 of the handle 864 such that the lumen of the tubular member 862 is coextensive with the lumen of the handle 864. As discussed above, the tubular member 862 can also extend at least partially or fully through the lumen 870 of the handle 864.

The handle 864 can comprise a moveable portion or arm 880. The arm 880 can comprise a proximal portion and a distal portion. In accordance with some embodiments, arm 880 can be formed unitarily with the handle 864, as a single, continuous piece of material. However, in some embodiments, the arm 880 can be formed as a separate component from the handle 864 and coupled thereto. The handle 864 can comprise a hinge 882 that couples the arm 880 to the handle 864. The hinge 882 can be coupled to the proximal or distal portion of the arm 880 in order to couple the arm 880 to a proximal or distal portion of the handle 864. FIG. 6 shows the pivotal coupling of the distal portion of the arm 880 to the distal portion of the handle 864. The hinge 882 can be configured to permit the arm 880 to pivot about the hinge 882, relative to a longitudinal axis of the lumen 870. The hinge 882 can comprise a living hinge, a pivot hinge, and/or a strap. The hinge 882 can provide a resilient or biasing force that urges the arm 880 from a first position to a second position. For example, the embodiment illustrated in FIGS. 5 and 6 is configured such that the hinge 882 urges the arm 880 from an engaged position toward a disengaged position.

In any such configuration, the hinge 882 can permit the arm 880 to be moveable relative to handle 864 to cause a portion of the arm 880 to pinch or engage a portion of the needle 866 extending through the lumen 870. For example, the arm 880 can comprise an inner surface that faces the lumen 870 of the handle 864. The inner surface can comprise an engagement surface 884 configured to extend along the lumen 870, or extend into the lumen 870 when the arm 880 is moved or compressed toward the handle 864. In some embodiments, a portion of the engagement surface 884 can form a portion of the lumen 870 through the handle 864. The engagement surface 884 can comprise a concave surface. In some embodiments, the engagement surface 884 can be engaged against the outer surface of the tubular member 862 to compress the corresponding portion of the tubular member 862, thereby reducing the cross-sectional or pass-through clearance of the tubular member 862 to engage the needle 866 disposed therein.

The arm 880 of the insertion device 860 can be movable between a disengaged configuration and an engaged configuration relative to the needle 866. In the disengaged configuration, a portion of the arm 880 can be separated or spaced apart from the handle 864 with the engagement surface 884 positioned along the lumen. For example, the arm 880 can be spaced apart from the handle 864 by a channel 890 that extends between the arm 880 and handle 864. The channel 890 can extend between an outer surface of the handle 864 and the inner surface of the arm 880. The channel 890 can extend from an outer surface of the handle 864 and intersect the lumen 870. The channel 890 can extend along a portion of the longitudinal length of the lumen 870. A portion of the channel 890 can extend through a plane that is transverse to the longitudinal axis of the lumen 870. Movement of a needle 866 positioned in the lumen 870 is permitted relative the longitudinal axis of the lumen 870, in the disengaged configuration.

In some embodiments, the channel 890 can comprise a groove or notch 886 configured to facilitate pivoting of the arm 880 relative to the handle 864. The notch 886 can extend into the inner surface of the arm 880 or hinge 882. The notch 886 can be positioned proximally of the distal portion of the arm 880. The notch 886 can provide advantageous flexibility for the device 860 while allowing the arm 880 to rebound from an engaged configuration.

The needle 866 can be positioned within the lumen 870 of the handle 864, such that a proximal portion of the needle 866 extends within the lumen 870, and a distal portion of the needle 866 extends out of the lumen 870, distal to the distal portion of the handle 864. The thread 80 can extend within the lumen of tubular member 862, from the proximal portion of the needle 866 toward the proximal portion of the tubular member 862.

In the engaged configuration, the arm 880 can be urged toward the handle 864 so that a portion of the arm 880 extends into the lumen 870 to decrease a cross-sectional profile of the lumen. The arm 880 can be pivoted toward the lumen 870 to move the engagement surface 884 into the outer surface of tubular member 862, such that the inner surface of tubular member 862 extends into the lumen 870.

In the disengaged configuration, the engagement surface 884 can be separated or spaced apart from a surface of the handle 864, opposing the engagement surface 884, by a first distance. The first distance can be approximately equal to or greater than a distance across the outer cross-sectional profile of the lumen 870 or tubular member 862, such that the engagement surface 884 extends along the lumen 870 and movement of a needle 866 is permitted. In the engaged configuration, the engagement surface 884 can be moved into the lumen 870 toward the surface of the handle, opposing the engagement surface 884, such that the engagement surface 884 is separated or spaced apart from the opposing handle surface by a second distance. The second distance can be approximately equal to or less than a distance across the outer cross-sectional profile of the lumen 870 or tubular member 862, such that the engagement surface 884 extends into the lumen 870 and movement of a needle 866 is restricted.

To insert the needle 866 and thread 80 into the patient, the insertion device 860 can be moved to the engaged configuration to engage and prevent axial movement of the needle 866. The insertion device 860 can be directed toward a patient's skin so that the distal portion of the needle 866 pierces the skin and permits movement of the needle 866 into the patient.

Further insertion of the needle 866 and thread 80 into the patient can be achieved by returning the insertion device 860 to the disengaged configuration. The insertion device 860 can be returned to the disengaged configuration by releasing the arm 880 to permit the engagement surface 884 to move away from the lumen 870 or tubular member 862. The insertion device 860 can be moved toward the proximal portion of the needle 866 and the arm 880 biased toward the tubular member 862, such that the engagement surface 884 or tubular member 862 engages the needle 866.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A thread insertion assembly comprising: a tubular member comprising a proximal portion, a distal portion, and a lumen extending between the proximal and distal portions; and a handle comprising a body component coupled to the tubular member, the body component comprising a passage that extends in communication with the lumen, the handle further comprising first and second arms coupled to the body component and extending outwardly from the distal portion of the tubular member; wherein in a first configuration, the first and second arms are positioned along the passage to define a first cross-sectional clearance, and in a second configuration, a portion of at least one of the first or second arms extends along the passage to define a second cross-sectional clearance, different from the first cross-sectional clearance, to change a cross-sectional profile of the passage.

Clause 2. The thread insertion assembly of Clause 1, wherein the tubular member is compressed by the portion of at least one of the first or second arms in the second configuration.

Clause 3. The thread insertion assembly of any one of the preceding Clauses, comprising a trocar positioned within the passage, wherein in the second configuration, the trocar is engaged by the first arm or the second arm.

Clause 4. The thread insertion assembly of Clause 3, comprising a thread coupled to the trocar, wherein the thread extends along the proximal portion of the tubular member.

Clause 5. The thread insertion assembly of any one of the preceding Clauses, wherein the second cross-sectional clearance is less than the first cross-sectional clearance.

Clause 6. The thread insertion assembly of any one of the preceding Clauses, wherein the first arm or second arm is biased toward the first configuration.

Clause 7. The thread insertion assembly of any one of the preceding Clauses, wherein the tubular member extends through the passage and in the second configuration, the portion of at least one of the first or second arms compresses the lumen to decrease a cross-sectional profile of the lumen.

Clause 8. The thread insertion assembly of any one of the preceding Clauses, comprising a cap comprising a proximal portion, a closed distal portion, and a cavity extending from the proximal portion toward the distal portion, wherein the proximal portion is configured to couple to a distal portion of the tubular member to enclose the lumen.

Clause 9. The thread insertion assembly of any one of the preceding Clauses, wherein each of the first and second arms comprise a proximal portion coupled to the handle, and a distal portion comprising a grasping surface.

Clause 10. The thread insertion assembly of Clause 9, wherein the grasping surface extends transverse to the respective first or second arm.

Clause 11. The thread insertion assembly of Clause 9, wherein each grasping surface extends parallel to the passage.

Clause 12. The thread insertion assembly of any one of Clauses 9 to 11, wherein each grasping surface comprises a ridge on a surface facing away from the passage.

Clause 13. The thread insertion assembly of any one of the preceding Clauses, wherein passage comprises a tubular lumen.

Clause 14. A thread insertion assembly comprising: a tubular member comprising a proximal portion, a distal portion, and a lumen extending between the proximal and distal portions; and a handle coupled to the tubular member distal portion, the handle comprising a passage that extends in communication with the lumen and a moveable arm having an inner surface forming a portion of the passage, the moveable arm having (i) a first position in which an inner surface of the arm is positioned along the passage to define a first cross-sectional clearance and (ii) a second position in which a portion of the arm extends along the passage to define a second cross-sectional clearance, different from the first cross-sectional clearance, to change a cross-sectional profile of the passage.

Clause 15. The thread insertion assembly of Clause 14, wherein the arm is pivotably coupled to the handle.

Clause 16. The thread insertion assembly of any one of Clauses 14 to 15, wherein the arm and the handle are formed as a single, continuous structure.

Clause 17. The thread insertion assembly of any one of Clauses 14 to 16, wherein the arm is pivotably coupled to the handle by a living hinge.

Clause 18. The thread insertion assembly of any one of Clauses 14 to 17, wherein the inner surface of the arm comprises a concave surface.

Clause 19. The thread insertion assembly of any one of Clauses 14 to 18, comprising a trocar positioned within the passage, wherein in the second position, the trocar is engaged by the arm.

Clause 20. The thread insertion assembly of any one of Clauses 14 to 19, comprising a thread coupled to the trocar, wherein the thread extends along the proximal portion of the tubular member.

Clause 21. The thread insertion assembly of any one of Clauses 14 to 20, wherein the arm is separated from the handle by a channel extending from an outer surface of the handle to the passage, and along a portion of a length of the handle.

Clause 22. The thread insertion assembly of Clause 21, wherein a portion of the channel extends through a plane transverse to a longitudinal axis of the passage.

Clause 23. A method of inserting a thread comprising: positioning a portion of a trocar between first and second arms of a handle; biasing at least one of the first and second arms such that a portion of the at least one of the first and second arms engages a proximal portion of the trocar such that movement of the trocar, relative to the handle, is restricted; inserting a distal portion of the trocar into a patient; releasing at least one the first and second arms to release the trocar such that movement of the trocar, relative to the handle, is permitted; and retracting the handle relative to the patient.

Clause 24. The method of Clause 23, comprising positioning the trocar between first and second arms of a handle such that the distal portion of the trocar extends from the handle.

Clause 25. The method of any one of Clauses 23 to 24, wherein inserting a portion of the trocar into a patient comprises moving the handle toward the patient.

Clause 26. A method of inserting a thread comprising: positioning a trocar within a passage of a handle such that a proximal portion of the trocar is aligned with a portion of the handle comprising a moveable arm having an inner surface forming a portion of the passage; biasing the arm toward the body such that a portion of the arm engages a proximal portion of the trocar within the passage such that movement of the trocar, relative to the handle, is restricted; inserting a distal portion of the trocar into a patient; releasing the arm to release the trocar such that movement of the trocar, relative to the handle, is permitted; and retracting the handle relative to the patient.

Clause 27. The method of Clause 26, comprising positioning the trocar within the handle such that the distal portion of the trocar extends from the handle.

Clause 28. The method of any one of Clauses 26 to 27, wherein inserting a portion of the trocar into a patient comprises moving the handle toward the patient.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A thread insertion assembly comprising:
  a tubular member comprising a proximal portion, a distal portion, and a lumen extending between the proximal and distal portions;
  a handle comprising a body component coupled to the tubular member, the body component comprising a passage that extends in communication with the lumen, the handle further comprising first and second arms coupled to the body component and extending outwardly from the distal portion of the tubular member; and
  a trocar positioned within the passage;

wherein in a first configuration, the first and second arms are positioned along the passage to define a first cross-sectional clearance, and in a second configuration, a portion of at least one of the first or second arms extends along the passage to define a second cross-sectional clearance, different from the first cross-sectional clearance, to change a cross-sectional profile of the passage and to engage against the trocar to resist movement thereof relative to the handle.

2. The thread insertion assembly of claim 1, wherein the tubular member is compressed by the portion of at least one of the first or second arms in the second configuration.

3. The thread insertion assembly of claim 1, wherein, in the first configuration, the handle is proximally slideable relative to the trocar to separate the handle from the trocar.

4. The thread insertion assembly of claim 1, comprising a thread coupled to the trocar, wherein the thread extends along the proximal portion of the tubular member.

5. The thread insertion assembly of claim 4, wherein a distal end portion of the thread is coupled to a proximal portion of the trocar.

6. The thread insertion assembly of claim 1, wherein the second cross-sectional clearance is less than the first cross-sectional clearance.

7. The thread insertion assembly of claim 1, wherein the first arm or second arm is biased toward the first configuration.

8. The thread insertion assembly of claim 1, wherein the tubular member extends through the passage and in the second configuration, the portion of at least one of the first or second arms compresses the lumen to decrease a cross-sectional profile of the lumen.

9. The thread insertion assembly of claim 1, wherein the lumen extends between the first and second arms.

10. The thread insertion assembly of claim 1, wherein the body comprises proximal and distal portions of the handle.

11. The thread insertion assembly of claim 10, wherein the first and second arms are coupled to the proximal portion of the body.

12. The thread insertion assembly of claim 1, wherein each of the first and second arms comprise a proximal portion coupled to the handle, and a distal portion comprising a grasping surface.

13. A method of inserting a thread comprising:
providing a tubular member comprising a proximal portion, a distal portion, and a lumen extending between the proximal and distal portions, a handle coupled to the distal portion of the tubular member, the handle comprising a body component having a passage that extends in communication with the lumen, and first and second arms coupled to the body and extending outwardly from the distal portion of the tubular member, the first and second arms having an inner surface forming a portion of the passage, (i) a first position in which the first and second arms are positioned along the passage to define a first cross-sectional clearance, and (ii) a second position in which a portion of the first or second arms extend along the passage to define a second cross-sectional clearance, different from the first cross-sectional clearance, to change a cross-sectional profile of the passage;
positioning a trocar within the passage while the first or second arm is in the first position;
moving the first and second arms to the second position to engage the trocar relative to the handle and resist movement of the trocar relative to the handle;
inserting the trocar into a patient;
releasing the first or second arm from the second position to release the trocar and permit movement of the trocar relative to the handle; and
proximally retracting the handle relative to the trocar and the patient to separate the handle from the trocar.

14. The method of claim 13, wherein the positioning comprises positioning the trocar within the passage such that a distal portion of the trocar extends out of the passage.

15. The method of claim 13, wherein the inserting comprises moving the handle toward the patient.

16. The method of claim 13, wherein the moving the first and second arms to the second position comprises compressing the trocar between the first and second arms.

17. The method of claim 13, wherein the inserting the trocar comprises distally moving a thread coupled to the trocar into the patient.

18. The method of claim 13, further comprising separating the thread from the trocar.

* * * * *